US00PP33261P2

(12) United States Plant Patent

Van Swieten

(10) Patent No.: US PP33,261 P2
(45) Date of Patent: Jul. 13, 2021

(54) PHALAENOPSIS ORCHID PLANT NAMED 'PHALCHORBE'

(50) Latin Name: ***Phalaenopsis* hyrbid**
Varietal Denomination: PHALCHORBE

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/016,639

(22) Filed: Sep. 10, 2020

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALCHORBE', particularly characterized by white, flecked flowers with yellow-white lips, convex flower shape in lateral view, dark red calluses, and is propagated by meristem tissue culture, is disclosed.

3 Drawing Sheets

Genus and species: *Phalaenopsis* hybrid.
Variety denomination: 'PHALCHORBE'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALCHORBE'.

The new *Phalaenopsis* plant is a product of a planned breeding program conducted by the inventor in Bleiswijk, the Netherlands. The objective of this breeding program was to create a new *Phalaenopsis* plant with many attractive, white, flecked flowers with yellow and white lips, suitable for potted plant production.

The new *Phalaenopsis* plant 'PHALCHORBE' is a result of cross-pollination made by the inventor in October 2011 in Bleiswijk, the Netherlands, of the proprietary female, or seed parent, *Phalaenopsis* hybrid '6240-02' (unpatented) with the proprietary male, or pollen parent, *Phalaenopsis* hybrid '35069-01' (unpatented).

The new *Phalaenopsis* was selected by the inventor as a single plant within the progeny of the stated cross-pollination in a controlled greenhouse in Bleiswijk, the Netherlands, in August 2014. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 23, 2019 (Application no. 2019/2370), by Applicant who obtained the subject matter disclosed directly from the inventor. 'PHALCHORBE' has not been made publicly available or sold anywhere in the world prior to the effective filing date of this application with the exception of sales or disclosures made one year or less before the effective filing date of this claimed invention by Applicant who obtained 'PHALCHORBE' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALCHORBE' as a new and distinct variety of *Phalaenopsis* plant:

1) White, flecked flowers with yellow-white lips;
2) Flower shape in lateral view is convex; and
3) Callus is dark red.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in August 2020. Colors in the photographs may differ from the color values cited in the detailed botanical description, which accurately describe the actual colors of the new variety.

DESCRIPTION OF THE NEW VARIETY

Figure 1:
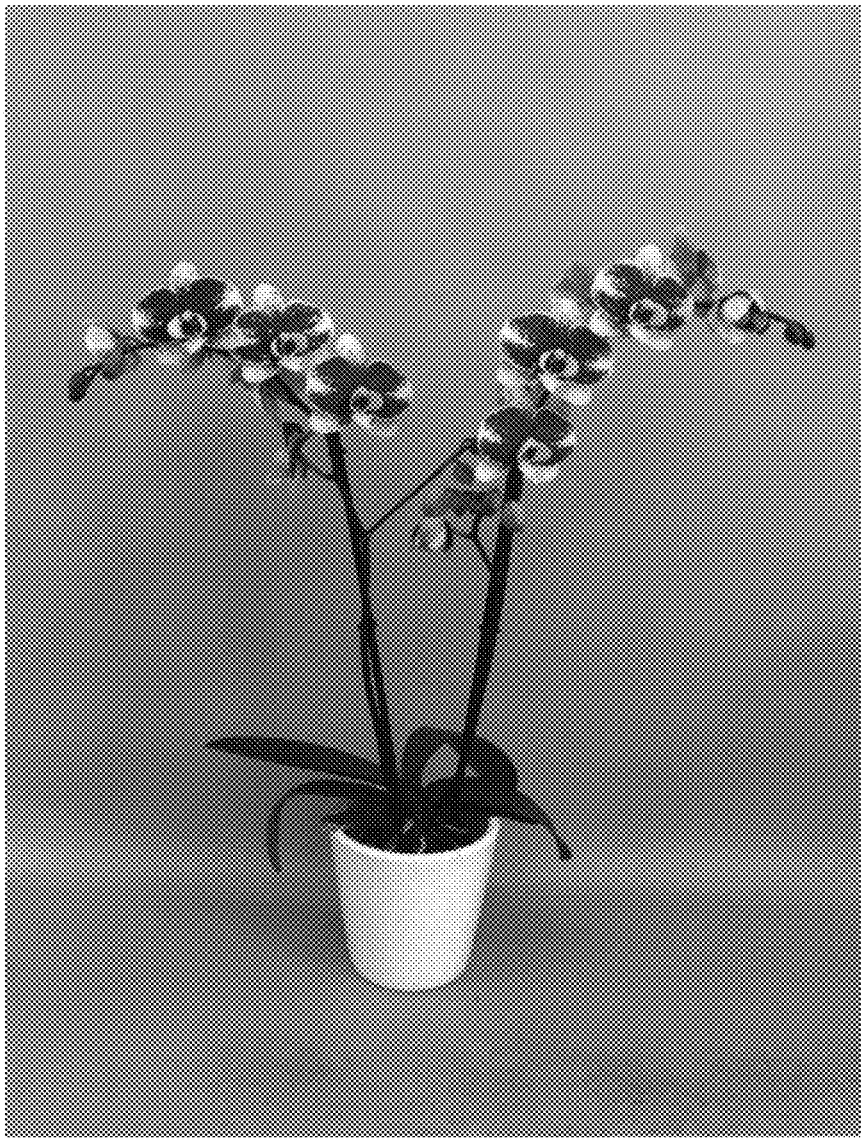
FIG. 1 shows the overall plant habit, including blooms, buds, and foliage of 'PHALCHORBE'.
Figure 2:
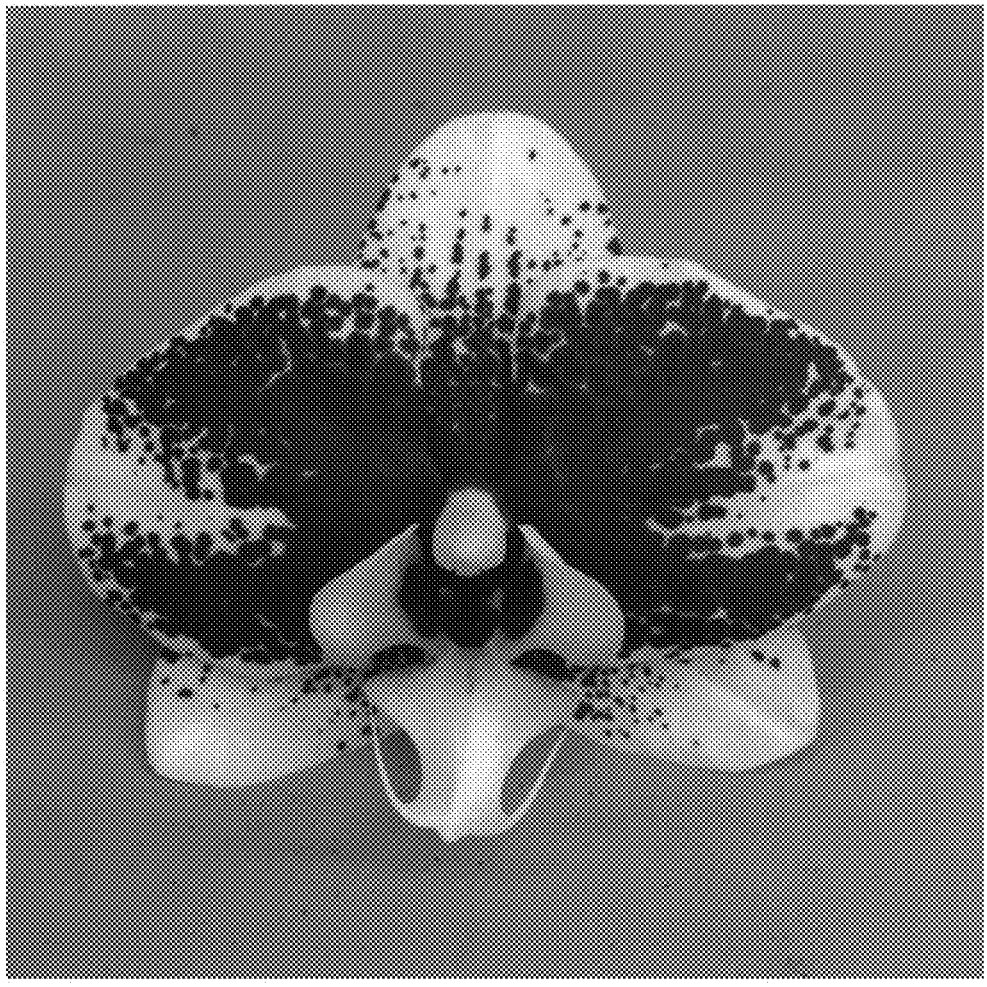
FIG. 2 shows a close-up of a flower of 'PHALCHORBE'.
Figure 3:
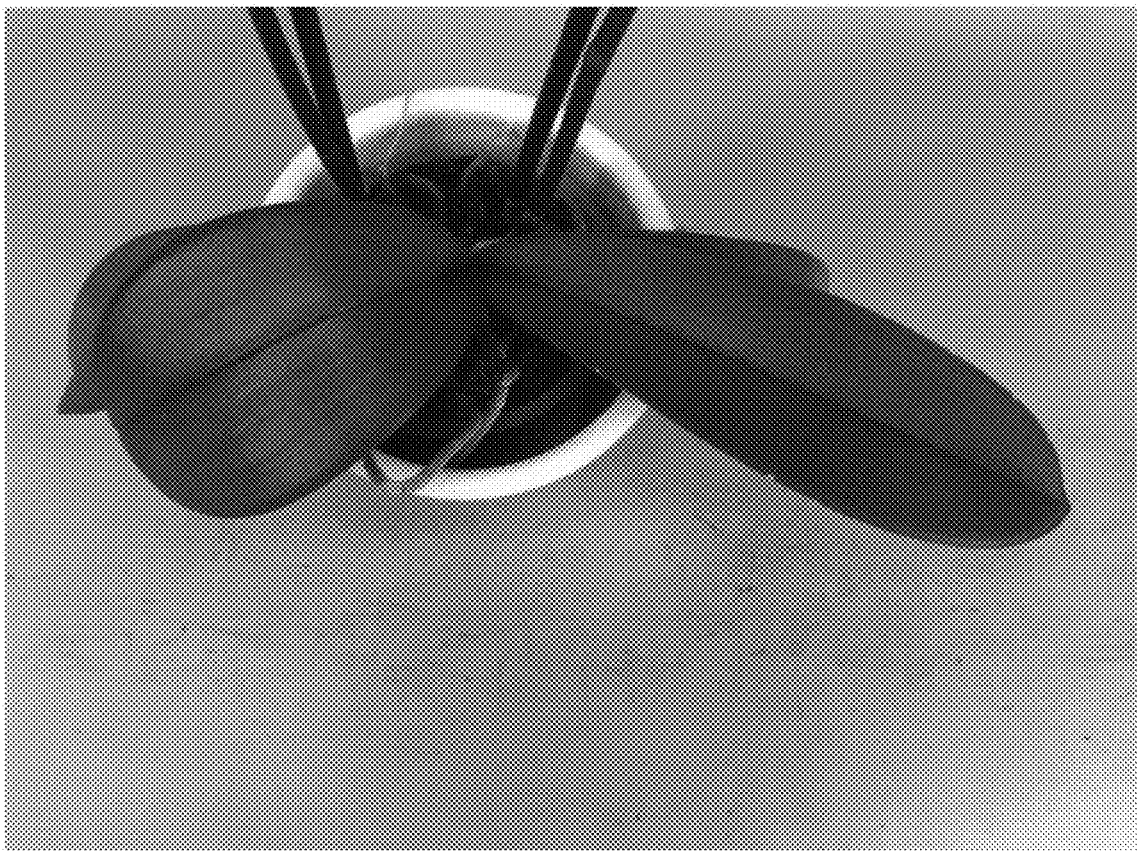
FIG. 3 shows an overhead view of the leaves of 'PHALCHORBE'.

The following detailed description sets forth the distinctive characteristics of 'PHALCHORBE'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in August 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALCHORBE'.

Parentage:

*Female parent*.—*Phalaenopsis* cultivar '6240-02' (unpatented).

*Male parent*.—*Phalaenopsis* cultivar '35069-01' (unpatented).

Propagation:

*Type*.—Meristem tissue culture.

Roots:

*Root description*.—Greyed-green (a color in between RHS 190B and 190C) colored roots with branching lateral roots having yellow-green (a color in between RHS N144A and 144C) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 55.0 cm to 60.0 cm.

*Width* (*measured from leaf tips*).—About 32.0 cm to 34.0 cm.

*Vigor*.—Strong.

Leaves:

*Mature leaves*.—Quantity per plant: 6 to 7 leaves are produced before flowering. Length (fully expanded): 17.0 cm to 19.0 cm. Width: 6.0 cm to 8.0 cm. Position of the broadest part of the leaf: Toward the apex. Shape: Obovate. Base shape: Moderately elongated. Apex: Obtuse unequal. Leaf blade angle with the petiole (measured from the horizontal position): Between 10 degrees and 25 degrees. Leaf margin: Entire. Color: Upper surface: RHS 146A with a touch of reddish-brown (RHS 200B) at margin. Lower surface: RHS 146B with a dark red-brown margin (a color in between RHS 187B and 200B). Texture (both upper and lower surfaces): Smooth. Thickness: 2.4 mm to 2.6 mm. Variegation: Absent. Venation: Pattern: Parallel. Color of the midvein: Upper surface: RHS 146A with a touch of reddish-brown (RHS 200B) toward the tip. Lower surface: Dark red-brown (a color in between RHS 187B and 200B).

Peduncle:

*Quantity per plant*.—1 to 2.

*Number of flowers per peduncle*.—14 to 20.

*Length*.—55.0 cm to 60.0 cm.

*Diameter*.—5.0 mm to 6.0 mm.

*Strength*.—Strong.

*Aspect*.—Upright to slightly pendent.

*Texture*.—Smooth.

*Color*.—Mix of reddish-brown (RHS 200B) and green (RHS 146C).

*Internode length*.—4.0 cm to 5.0 cm.

Inflorescence description:

*Appearance*.—Upright to slightly pendent, panicle inflorescence with bilaterally symmetrical flowers that open in succession beginning with the lowermost flower.

*Number of inflorescences*.—1 to 2.

*Inflorescence size*.—Height (from base to tip): 300.0 mm to 350.0 mm.

*Flowering time*.—First flowers can be expected 10 to 11 months after planting in a 12-cm pot.

*Flower*.—Height: 73.0 mm to 78.0 mm. Diameter: 85.0 mm to 90.0 mm. Depth of lip: 26.0 mm to 28.0 mm.

*Flower longevity*.—On the plant: 9 to 11 weeks.

*Flower shape*.—Convex.

*Fragrance*.—Absent.

*Flower bud*.—Average size: Medium to large. Length: 21.0 mm to 23.0 mm. Width: 17.0 mm to 19.0 mm. Shape: Egg shaped. Color: Yellow-green (RHS 145B) and purplish-red (RHS N77B) toward the tip.

*Petals*.—Arrangement: Open/free. Shape: Semi-circular. Apex: Emarginated asymmetric. Margin: Weakly undulated. Length (from base to tip): 39.0 mm to 41.0 mm. Width: 46.0 mm to 48.0 mm. Position of the broadest part of the petal: Toward the base. Color (when fully opened): Upper surface: Basic color: White (RHS NN155C). Over color: Dark red-purple flecks (a color in between RHS N78A and N79C) toward base. Lower surface: Basic color: White (RHS NN155C). Over color: Diluting reddish-purple flecks (RHS N79D). Number of spots, flecks, and stripes on the petals (upper surface): Many to very many flecks toward base. Color of spots, flecks, and stripes on the petals (upper surface): A color in between RHS N78A and N79C. Density of netting of the petals (upper surface): None. Color of the netting (upper surface): None.

*Dorsal sepal*.—Shape: Elliptic. Apex: Rounded. Margin: Entire. Length (from base to tip): 44.0 mm to 46.0 mm. Width: 28.0 mm to 30.0 mm. Position of the broadest part of the dorsal sepals: At the middle. Color (when fully opened): Upper surface: Basic color: White (RHS NN155C). Over color: Dark red-purple flecks (a color in between RHS N78A and N79C) toward base. Lower surface: Basic color: Very light purple (RHS 76B). Over color: Light reddish-purple (RHS N78D) and diluting reddish-purple flecks (RHS N79D). Number of spots, flecks, and stripes on the dorsal sepals (upper surface):

Many flecks toward the base. Color of spots, flecks, and stripes on the dorsal sepals (upper surface): A color in between RHS N78A and N79C. Density of netting of the dorsal sepals (upper surface): None. Color of the netting: Not applicable.

*Lateral sepals*.—Shape: Ovate. Apex: Obtuse asymmetric. Margin: Entire. Length (from base to tip): 43.0 mm to 45.0 mm. Width: 25.0 mm to 27.0 mm. Position of the broadest part of the lateral sepals: Toward the base. Color (when fully opened): Upper surface: Basic color: White (RHS NN155C). Over color: Dark red-purple flecks (a color in between RHS N78A and N79C) toward base. Lower surface: Basic color: Very light purple (a color in between RHS 76B and 76C). Over color: Touch of yellow-green (RHS 145D) at the base; purplish-pink midvein (RHS N78C) toward the tip; diluting flecks (RHS N79D). Number of spots, flecks, and stripes on the lateral sepals (upper surface): Many flecks toward base. Color of spots, flecks, and stripes on the lateral sepals (upper surface): A color in between RHS N78A and N79C. Density of netting of the lateral sepals (upper surface): None. Color of the netting (upper surface): Not applicable.

*Labellum* (*lip*).—Whiskers: Present. Length of whiskers: 15.0 mm to 17.0 mm. Color of whiskers: White (RHS NN155C) at the base; light yellow (RHS 10C) toward the tip. Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated (widely wavy). Length: 20.0 mm to 22.0 mm. Width: 15.0 mm to 17.0 mm. Color: Upper surface: White (RHS NN155C) with yellow margin (RHS 9C) on one side toward the base. Lower surface: White (RHS NN155C) with diluting purplish-red fleck (RHS N77D) at the base; yellow margin (RHS 9B) on one side toward the base. Number of spots and stripes on the lateral lobe: Few stripes at the base. Color of spots and stripes on the lateral lobe: A color in between RHS N79B and N79C. Density of netting of the lateral lobe: None. Color of the netting: None.

*Apical lobe*.—Shape: Triangular. Margin: Entire. Length: 19.0 mm to 21.0 mm. Width: 20.0 mm to 22.0 mm. Color: Upper surface: Dark reddish-orange margin (RHS 175C) at the base; light yellow wings (a color in between RHS 9C and 9D) at the base; white (RHS NN155C) toward whiskers. Lower surface: Dark reddish-orange margin (RHS 175C) and diluting purplish-red (RHS N77B) at the base; light yellow wings (a color in between RHS 9C and 9D); white (RHS NN155C) toward whiskers. Number of spots and stripes on the apical lobe: None. Color of spots and stripes on the apical lobe: Not applicable. Density of netting of the apical lobe: None. Color of the netting: None.

*Callus*.—Average size: Medium. Height: 6.0 mm to 7.0 mm. Length: 5.0 mm to 6.0 mm. Width: 4.0 mm to 5.0 mm. Color: Dark red (RHS 187A); light yellow (RHS 10A) on sides toward the tip.

Reproductive organs:

*Column*.—Length: 9.0 mm to 11.0 mm. Diameter: 6.2 mm to 6.6 mm. Color: White (RHS NN155C) at the base with very light purple region (RHS 76B) toward the tip.

*Pollinia*.—Quantity: 2. Diameter: 0.8 mm to 1.0 mm. Color: Orange (RHS 25A).

*Ovary*.—Length: 14.0 mm to 16.0 mm. Diameter: 2.6 mm to 2.8 mm.

*Pedicel*.—Length: 46.0 mm to 48.0 mm. Diameter: 2.9 mm to 3.2 mm. Texture: Smooth. Color: Hint of dark purplish-red (RHS N79C) at the base; light yellow-green (RHS 145D) and light purple (RHS N75B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALCHORBE' differs from female parent plant '6240-02' (unpatented) in that 'PHALCHORBE' has flowers with a flecked pattern, calluses with a basic color of dark red, whiskers that are white at the base and light yellow toward the tip, and columns that are white at the base with very light purple region toward the tip, whereas '6240-02' has flowers with an even pattern, calluses with a basic color of yellow, whiskers that are reddish-purple, and columns that are reddish-purple.

'PHALCHORBE' differs from male parent plant '35069-01' (unpatented) in that 'PHALCHORBE' has apical lobes with a basic color of white, whiskers that are white at the base and light yellow toward the tip, and columns that are white at the base with very light purple region toward the tip, whereas '35069-01' has apical lobes with a basic color of reddish-purple, whiskers that are reddish-purple, and columns that are white with reddish-purple region at the middle.

'PHALCHORBE' is most similar to the commercial *Phalaenopsis* plants named 'PHALFOYX' (U.S. Plant Pat. No. 28,103) and 'PHALYDSAP' (U.S. Plant Pat. No. 29,388). 'PHALCHORBE' differs from the commercial variety 'PHALFOYX' in that 'PHALCHORBE' has flowers with a flecked pattern and rounded dorsal sepal apexes, whereas 'PHALFOYX' has flowers with a dotted/flecked and edged pattern and emarginated dorsal sepal apexes. Additionally, 'PHALCHORBE' has narrower petals than 'PHALFOYX'.

'PHALCHORBE' differs from the commercial variety 'PHALYDSAP' in that 'PHALCHORBE' has apical lobes with a main color of white, whiskers that are white at the base and light yellow toward the tip, and rounded dorsal sepal apexes, whereas 'PHALYDSAP' has apical lobes with a main color of red, whiskers that are red-purple with white tips, and obtuse dorsal sepal apexes.

I claim:

1. A new and distinct variety of *Phalaenopsis* plant named 'PHALCHORBE', substantially as described and illustrated herein.

* * * * *